US006839581B1

(12) United States Patent
El-Solh et al.

(10) Patent No.: US 6,839,581 B1
(45) Date of Patent: Jan. 4, 2005

(54) METHOD FOR DETECTING CHEYNE-STOKES RESPIRATION IN PATIENTS WITH CONGESTIVE HEART FAILURE

(75) Inventors: Ali El-Solh, West Seneca, NY (US); Brydon Grant, East Amherst, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 0 days.

(21) Appl. No.: 10/347,555

(22) Filed: Jan. 17, 2003

Related U.S. Application Data

(63) Continuation-in-part of application No. 09/829,695, filed on Apr. 10, 2001, now abandoned.
(60) Provisional application No. 60/437,948, filed on Jan. 2, 2003, and provisional application No. 60/195,804, filed on Apr. 10, 2000.

(51) Int. Cl.$^7$ ................................................ A61B 5/00
(52) U.S. Cl. ........................................ 600/324; 600/323
(58) Field of Search ................................ 600/322–324, 600/310, 331, 529; 128/925

(56) References Cited

U.S. PATENT DOCUMENTS

| | | | |
|---|---|---|---|
| RE35,122 E | * 12/1995 | Corenman et al. | .......... 600/324 |
| 5,575,285 A | * 11/1996 | Takanashi et al. | .......... 600/323 |
| 6,083,173 A | 7/2000 | Grant et al. | |
| 6,223,064 B1 | 4/2001 | Lynn et al. | |
| 6,290,654 B1 | 9/2001 | Karakasoglu | |
| 6,594,518 B1 | * 7/2003 | Benaron et al. | ............. 600/342 |

FOREIGN PATENT DOCUMENTS

WO    WO 00/19895    4/2000

OTHER PUBLICATIONS

Blackshear et al., *Nocturnal Dyspnea and Atrial Fibrillation Predict Cheyne–Stokes Respirations in Patients with Congestive Hearth Failure*, Arch Intern Med, Jun. 26, 1995, vol. 155(12), pp. 1297–1302.

Dowdell et al., *Cheyne–Stokes Respiration Presenting as Sleep Apnea Syndrome. Clinical and Polysomnographic Features.* Am Rev Respir Dis, Apr. 1990, vol. 141(4 Pt. 1), pp. 871–879.

Hanley et al. *Pathogenesis of Cheyne–Stokes Respiration in Patients with Congestive Heart Failure. RElationship to Arterial PCO2.* Chest, 1993, vol. 104, pp. 1049–1084.

Staniforth et al., *Nocturnal Desaturation in Patients with Stable Heart Failure*, Heart, Apr. 1998, vol. 79(4), pp. 394–399.

\* cited by examiner

*Primary Examiner*—Eric F. Winakur
*Assistant Examiner*—Matthew Kremer
(74) *Attorney, Agent, or Firm*—Hodgson Russ LLP

(57) ABSTRACT

The present invention provides a diagnostic tool for detection of Cheyne-Stokes Respiration (CSR). This invention also provides a method for development of the diagnostic tool. The method comprises the steps of performing overnight oximetry recordings in patients suspected of sleep disordered breathing. Spectral analysis is performed on the oximetry recordings to obtain a set of parameters which can be used in the construction of a classification tree and a trained neural network. The diagnostic tools of the present invention can be used for classification of a patient as having CSR or obstructive sleep apnea.

8 Claims, 9 Drawing Sheets

METHOD FOR DETECTING CHEYNE-STOKES RESPIRATION IN PATIENTS WITH CONGESTIVE HEART FAILURE

This application claims priority of U.S. provisional application Ser. No. 60/437,948, filed on Jan. 2, 2003 and is also a continuation-in-part of U.S. application Ser. No. 09/829,695 filed on Apr. 10, 2001 now abandoned which in turn claims priority of U.S. provisional application serial No. 60/195,804 filed on Apr. 10, 2000, the disclosures of which is incorporated herein by reference.

FIELD OF THE INVENTION

The present invention relates generally to the field of sleeping disordered breathing. More particularly, the present invention provides a diagnostic tool to diagnose Cheyne-Stokes respiration (CSR), and a method for developing such a diagnostic tool.

DISCUSSION OF RELATED ART

Sleep disordered breathing (SDB) is estimated to occur in about 60% of patients suffering from congestive heart failure (CHF; Rechtschaffen A, Kales A, eds. *A Manual of Standardized Technology, Techniques and Scoring System for Sleep Stages of Human Subjects*. Los Angeles: UCLA Brain Information Service/Brain Research Institute, 1968). Cheyne-Stokes respiration (CSR) is by far the most common form of SDB encountered with an estimated prevalence of 40% (Javaheri et al., 1995, *Ann Intern Med.*, 122:487–92; Findley et al., 1985, *South Med. J.*, 78:11-5). It is characterized by rhythmic rises and falls in tidal volume and breathing frequency that lead to oxygen desaturation, increased arousals, poor sleep quality, and altered sleep architecture. These features result in complaints of daytime somnolence, fatigue, and insomnia.

The pathophysiology of CSR is not completely understood, but it has become more apparent that the effect of altered breathing patterns may extend beyond the deterioration in psycho-cognitive function. The increase in urinary and plasma norepinephrine levels in patients with left ventricular failure (LVF) and CSR compared to those with CSR alone has been implicated in an accelerated loss of cardiac function, and an increased risk of death and cardiac transplantation (Naughton et al., 1995, *Am J Respir Crit Care Med*, 152:473–79; Hanly et al., 1996, *Am J Respir Crit Care Med*, 153:272–76). Nasal continuous positive airway pressure (CPAP) has been advocated as an effective nonpharmacological treatment for patients with congestive heart failure and CSR. Recent studies have shown that CPAP can abolish CSR, improve respiratory muscle strength (Granton et al., 1996, *Am J Respir Crit Care Med*, 153:277–82), and increase left ventricular ejection fraction (Naughton et al., 1993, *Am Rev Respir Dis*, 148:330–38), and may increase transplant-free survival.

The presence of CSR has been implicated in the increased mortality up to 56% over a 3 year-period compared to 11% in patients without CSR despite similar cardiac functional status and left ventricular function (Hanly et al., 1996, supra). Since nasal CPAP therapy was found to have a beneficial acute and chronic cardiovascular effect, early implementation might well be translated into improved cardiac function, reduced hospitalization and potentially reduced mortality.

In the absence of a good and accurate screening test, overnight polysomnography remains the gold standard test for the diagnosis of CSR. However, overnight polysomnography is an expensive, labor intensive and time-consuming procedure. Home pulse oximetry has been proposed as an alternative tool for identification CSR, but relies on visual inspection of the oximetry signal by a trained observer (Staniforth et al., 1998, *Heart*, 79:394–99).

Previous studies have reported the use of spectral analysis of heart rate variability in sleep disordered breathing (Khoo et al., 1999, *Sleep*, 22, 443–451; Berger et al., 1986, *IEEE Trans Biomed Eng*, 33, 900–904.). However, none were developed for the purpose of identifying patients with CSR-CSA. A recent study of 104 subjects with CHF by Staniforth et al. (1998, *Heart*, 79, 394–399.) has examined the desaturation index recorded in nocturnal oximetry (number of events of oxygen desaturation $\geq 4\%$ from baseline per hour of sleep) compared to normal controls. With a threshold of 15 dips per hour, the model yielded a specificity of 81% and a sensitivity of 87% for detecting CSR-CSA. However, the overall accuracy of the model was not provided. Those authors made no attempt to determine if pulse oximetry could be used to distinguish between CSR-CSA and OSA. Takanashi et al. (U.S. Pat. No. 5,575,285) describe measuring oxygen saturation in blood from scattered and transmitted light and performing Fourier transformation to obtain a power spectrum over a frequency range of 500 Hz to 20 kHz. However, this method does not allow distinction between patients with CSR and OSA.

Thus, there is an ongoing need for more accurate methods in the detection of Cheyne-Stokes respiration.

SUMMARY OF THE INVENTION

The present invention provides a method for developing a diagnostic tool for the identification of CSR. The present invention also provides a diagnostic tool and a method for using the diagnostic tool for identification of CSR in an individual.

In one embodiment, the diagnostic tool comprises a classification tree. The method for developing the classification tree comprises the steps of performing clinical studies on patients suspected of having sleep disordered breathing with some having obstructive sleep apnea. Based on the clinical studies, patients are identified as having or not having CSR. Overnight pulse oximetry recordings are obtained from these individuals following which spectral analysis is performed on the oximetry recordings. From the spectra, a set of parameters or key features are determined and used to build a classification tree that enables the prediction of CSR. The tree is tested by cross validation with clinical diagnosis.

The diagnostic method for detecting the presence or absence of CSR in an individual comprises the steps of obtaining overnight oximetry recordings from the individual, performing spectral analysis of the recordings, obtaining a set of parameters or key features from the spectra and inputting the parameters into a classification tree to obtain diagnosis whether an individual has CSR or not.

In another embodiment, the diagnostic tool is a trained neural network. The method for developing a trained neural network comprises performing clinical studies to identify patients having sleep disordered breathing with some having obstructive sleep apnea. Overnight pulse oximetry readings are obtained from those individuals and a power spectrum is obtained. From the spectra and from the overnight oximetry readings, a set of parameters is obtained and input into a neural network. The neural network analyzes the parameters and develops mathematical relationships between the parameters. The output based on the mathematical relationships is compared to the actual diagnosis and used to train the network. A set of relationships which produces the smallest error, are obtained and validated to obtain a trained neural network.

The trained neural network obtained above can be used for diagnosis of a patient with CSR. An algorithm was developed to processes the data from overnight oximetry and analyze the spectral analysis to obtain the frequency and the magnitude at the highest and next highest local maxima. These parameters are then fed into the neural network and provides an output that classifies a patient as having CSR, OSA or no breathing disorder.

DETAILED DESCRIPTION OF THE INVENTION

The present invention provides a method for developing a diagnostic tool for identification of patients with CSR and a method for using the diagnostic tool to diagnose the presence or absence of CSR in an individual.

The present method is based on the observation that when oxygen saturation levels over selected time intervals are transformed to frequency distribution spectra, the spectral indices for those patients with CSR display characteristic features with distinctive discriminative attributes compared to other sleep disordered breathing. While the power frequency distribution (a plot of variance versus frequency) of normal subjects was shown to have no apparent peak, and of OSA patients to have broad-band peaks, the patients with congestive heart failure having CSR often had a unique distribution of spectral peaks conforming to a long-period oscillating output.

In one embodiment, the diagnostic tool is a classification tree that can used to identify CSR. For developing the classification tree, individuals with suspected sleep apnea are identified from clinical sleep studies. Overnight oximetry recordings are obtained from individuals suspected of having OSA. Power spectra are generated from the oximetry recordings. A set of key features or parameters are obtained from the power spectra. These parameters are then used as input data to construct a classification tree.

The present invention also provides a method of using the classification tree for identification of CSR. The method comprises performing spectral analysis of overnight pulse oximetry data. The spectral data is then analyzed using a classification tree to obtain a predictive value that is indicative of the likelihood that an individual has CSR.

Figure 1:
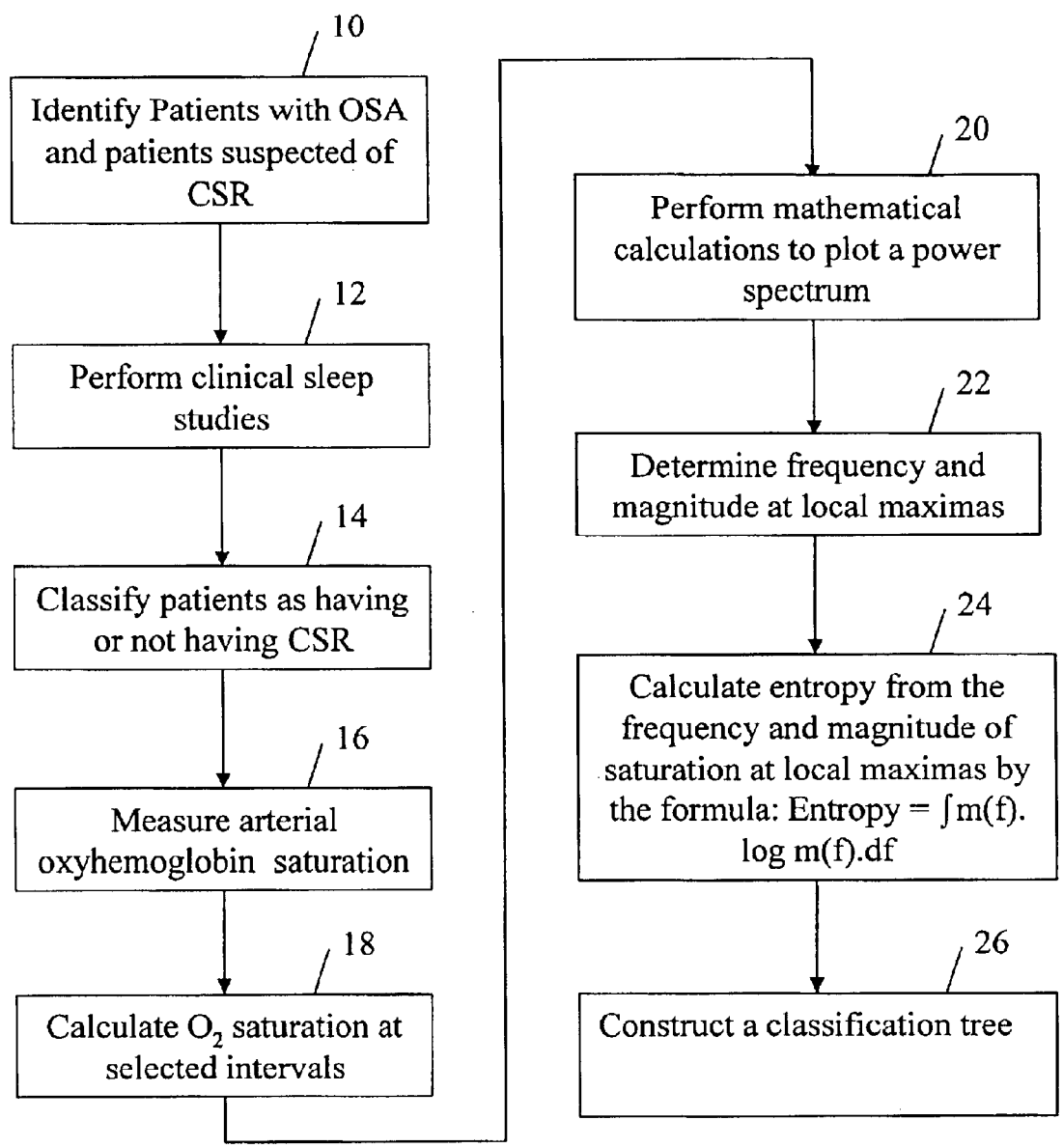
FIG. 1 is a representation of the steps for developing a classification tree according to the present invention.

The present invention is also directed to a software storage device such as a floppy disk, hard drive, a CD, a zip drive etc. having thereon computer readable code for causing a computer to execute all or a substantial portion of diagnostic method using a classification tree as described herein. The method for developing a classification tree is illustrated by the steps shown in FIG. 1 and is also illustrated by way of an example described below under Example 1.

In another embodiment, the diagnostic tool is a trained neural network. The data obtained from the power spectra is used to construct a neural network which can be used to detect CSR. An illustrative example for this is provided in Example 2 below. For developing the trained neural network, individuals with sleep disordered breathing are identified. Overnight pulse oximetry recordings and polysomnography recordings are obtained. Power spectra are generated from the pulse oximetry recordings. A set of parameters is obtained from the power spectra and from the oximetry readings. Mathematical relationships are developed between the parameters. These parameters are used as input into a neural network which is then trained by adjusting the mathematical relationships according to the actual diagnosis from clinical studies of polysomnography. The set of mathematical relationships which produce the smallest error is selected and tested for validation to produce a trained neural network.

The present invention also provides a method of using the trained neural network for identification of CSR. The method comprises performing spectral analysis of overnight pulse oximetry data. The spectral data and the oximetry readings are processed to obtain the power spectral density by calculating maximum entropy on each segment. At each frequency, the mean power was calculated from the average of the power of all segments at that particular frequency. The salient features of the CSR-CSA power spectrum that were selected for further analysis were the frequency and the magnitude of the power attained at the highest local maximum (f1, m1), and the frequency and the magnitude of the power attained at the next highest local maximum (f2, m2). These parameters along with the delta index are used as input parameters into the trained neural network to obtain a classification of the individual as having CSR, OSA or no breathing disorder.

The present invention is also directed to a software storage device such as a floppy disk, hard drive, a CD, a zip drive etc. having thereon computer readable code for causing a computer to execute all or a substantial portion of diagnostic method using a trained neural network as described herein.

The present study shows the utility of an artificial neural network as a screening tool for detecting CSR-CSA. The overall accuracy of the neural network in classifying sleep disordered breathing stemms from delineating the various relationships among the multitude of input parameters selected. The present invention offers potentially an accurate and easily applicable tool to detect heart failure patients with CSR-CSA at a relatively low cost. The method for developing a classification tree is illustrated by the steps shown in FIG. 1 and is also illustrated by way of an example described below under Example 1. The method for developing a trained neural network is illustrated in Example 2 and the method of using the trained neural network for diagnosis of CSR is illustrated in Example 3.

EXAMPLE 1

For developing a classification tree, patients suspected of obstructive sleep apnea were identified (Step 10). An analysis of sleep studies (Step 12) was performed in 248 patients at the Sleep Laboratory at the Veterans Affairs (VA) Medical Center in Buffalo, N.Y. (n=45) and at the National Sleep Technologies Laboratory in Syracuse, N.Y. Patients with left ventricular failure had been studied in the sleep laboratory in Buffalo as part on another study on sleep disordered breathing in patients with left venticular failure. All patients in Syracuse sleep laboratory were suspected of obstructive sleep apnea syndrome.

All the sleep studies were performed between February 1998 and June of 1999. Continuous electroencephalogram, electrooculogram, electrocardiogram, and submental electromyogram were recorded on a 16-channel polygraph using standard techniques, and digitized on a computerized system. The sleep data collection system was Aquetron 1000P at the Buffalo VA and Healthdyne in Syracuse (Healthdyne 930, Pittsburgh, Pa.). Airflow was measured qualitatively by the sum of an oral-nasal thermistor (Graphic Control; Buffalo, N.Y.). Thoracoabdominal movements were recorded with an inductive plethysmograph in Buffalo (Respitrace, Ambulatory Monitoring, Ardsley, NY) and with peizoelectric method in Syracuse.

Sleep stages were scored in 30-sec epochs using the Rechtschaffen and Kales sleep scoring criteria (1968, *A Manual of Standardized Technology, Techniques and Scoring System for Sleep Stages of Human Subjects*. Los Angeles: UCLA Brain Information Service/Brain Research Institute). Each epoch was analyzed for the number of apneas, hypopneas, arousals, oxyhemoglobin desaturation, and disturbances in cardiac rate and rhythm. Apnea was defined as the absence of airflow for more than 10 seconds. Hypopnea was defined as a visible 20% reduction in the airflow lasting more than 10 seconds associated with either 4% oxygen decrease in arterial oxyhemoglobin saturation or an electroencephalographic arousal, or both. Central apneas were defined by the cessation of airflow for 10 seconds accompanied by an absence of chest wall movement. The apnea-hypopnea index (AHI) was defined as the number of apneas and hypopneas per hour of sleep. The presence of CSR was defined as a central apnea index of $\geq\geq 5$ per hour of sleep, in combination with the characteristic pattern of crescendo-decrescendo pattern of hyperpnea alternating with hypopneas. An arousal was defined as recommended by the American Sleep Disorders Association's position paper as a change in electroencephalogram rhythm for greater than 3 sec. (Guilleminault et al., 1992, *Sleep*, 15:173–84).

The frequency spectra of $SPO_2$ from the 23 patients with CSR was compared with the spectra of 203 patients suspected of obstructive sleep apnea, and a validated model to identify the patients with CSR was developed. The model was tested by determining its specificity in patients with left ventricular failure who did not have CSR (n=22).

Gated $^{99}Tc$ equilibrium radionuclide angiography obtained within 6 month of the diagnostic sleep study was used as an objective measurement of cardiac function in those with documented CSR on overnight polysomnography. The quantitation and reporting of left ventricular function were preformed by trained technicians and a nuclear medicine physician blinded to the patient's sleep study findings.

Of the 248 patients, 221 (89%) were men and 26 (11%) were female. Forty four patients had congestive heart failure with a mean left ventricular ejection fraction (LVEF) of 24.9±9.1%. The largest proportion of patients was in NYHA class 2 (57%). Fifteen patients were in NYHA class 3 (34%), while 4 (9%) were in NYHA class 4. The causes of LVF were attributed to ischemic heart disease in 82% of the cases, nonischemic dilated cardiomyopathy in 16%, and others in 2%. Baseline age, body mass index, and LVEF were similar between those who met the criteria for central sleep apnea and those who did not (Table 1).

TABLE 1

Characteristics of left ventricular failure patients with and without central sleep apnea.

|  | Central sleep apnea (n = 22) | No central sleep apnea (n = 22) |
|---|---|---|
| Age (years) | 71 ± 4 | 68 ± 9 |
| Body mass index* (kg/m²) | 24.2 ± 3.8 | 26.9 ± 4.1 |
| Left ventricular ejection fraction (%) | 23 ± 5.7 | 27 ± 6.2 |

*Body mass index is the weight in kilograms divided by the square of the height in meters.

Table 2 lists the characteristics of sleep and disordered breathing events and oxyhemoglobin saturation during sleep in those patients.

TABLE 2

Sleep studies characteristics of patients with left ventricular failure

|  | Central Apnea (n = 22) | No Central Apnea (n = 22) | p value |
|---|---|---|---|
| Total recording time (min) | 417 ± 48 | 453 ± 62 | 0.6 |
| Total sleeping time (min) | 282 ± 98.5 | 307 ± 54 | 0.4 |
| Sleep efficiency (%) | 66 ± 19 | 68 ± 32 | 0.7 |
| Arousal index (/h) | 23 ± 19 | 12 ± 8 | 0.04 |
| Apnea-hypopnea index (/h) | 32 ± 13 | 3.6 ± 2 | <0.01 |
| Central apnea index (/h) | 22.7 ± 14.6 | 0.7 ± 1.6 | <0.01 |
| $SpO_2$ baseline value (%) | 92 ± 2 | 94 ± 4 | 0.4 |
| $SpO_2$ lowest value (%) | 77 ± 9 | 89 ± 2 | <0.01 |
| % time $SpO_2$ < 90% | 34 ± 31 | 14 ± 6 | <0.01 |

$SPO_2$ is the oxygen saturation by pulse oximetry

Among patients with CSR, the mean central sleep index was 22.7±14.6. Arousal index was significantly higher, and arterial oxyhemoglobin desaturation was significantly lower in CSA patients compared to those without CSA, but the differences in total sleeping time, and sleeping efficiency were not statistically significant.

Of the 203 remaining patients referred for evaluation of sleep disorders, 152 had polysomnographic evidence of obstructive sleep apnea (OSA). Thirty seven (18%) had severe OSA with AHI >40/hr, 47 (23%) had moderate OSA with AHI ranging between 20 and 40/hr, and 68 (33%) had mild OSA with AHI between 5 and 20/hr.

Based on the clinical studies, individuals were classified as having or not having CSR (step 14). In the next step 16, measurement of arterial oxyhemoglobin saturation was performed with a pulse oximeter with the probe placed on the patient's finger. In Syracuse, oximetry data were recorded with two seconds sampling interval with the oximetry sampling rate of 300 Hz and the data smoothed with a moving average of 4 seconds. In Buffalo, the oximetry (Ohmeda 3720, Louisville, Colo.) data was sampled at 400 Hz and the data smoothed with a moving average of 3 sec.

The raw data was processed to remove any artifacts by eliminating all changes of oxygen saturation between consecutive sampling intervals of greater than 4% per second, and any oxygen saturation less than 20%. The lowest value of the oxygen saturation by pulse oximetry ($SpO_2$) over 4 seconds intervals was determined (Step 18) and used for spectral analysis. Only the longest section of data free of artifacts on each subject was used for spectral analysis. In the next step 20, a power spectral was generated using the maximum entropy method. This approach is well known to those skilled in the art. It differs from Fourier transform methods and is explained in detail in Press et al. (1989, *Numerical recipes NY*, Cambridge University Press Chapter 12, Fourier transform spectral methods, 381–453). The power spectrum provides a measure of the variability of oxygen saturation that occurs over a range of frequencies. The magnitude of that power is related to the variance (square of the standard deviation). To determine optimal model size that minimizes the tradeoff between increased accuracy and increasing the variance of the estimated spectrum, the Bayesian information criterion was used. (Hurvich et al., 1989, *Biometrika*, 76:297–307).

The next step (step 22) was to determine a set of parameters from the power spectra. The spectrum covered frequencies between 0.00125 and 0.125 Hz. The key features of the power spectrum that identified to characterize the spectra of CSRs were the frequency and the magnitude of the power attained at the highest local maximum (f1, m1), and the frequency and the magnitude of the power attained at the next highest local maximum (f2, m2). A local maxima of magnitude in the spectrum was identified when there were lower magnitudes at frequencies immediately above and below the particular frequency. The spectrum generated between 0.00125 and 0.125 Hz at 100 frequencies equispaced on a log scale. The absolute magnitude (m1 and m2) were also normalized by the variance (M1 and M2) and there values incorporated into the model. The spectra were also characterized by the amount of entropy (randomness) in the data.

In the next step (Step 24) the entropy was measured by $$\text{Entropy} = -\int (m(f) * \log m(f)).df$$

where ∫ is the summation of the magnitudes of the spectrum at equidistant intervals of frequency on a linear scale between 0.00005 and 0.05 Hz, and m(f) represents the magnitude at specific frequency f. Heuristically, the entropy has been interpreted as a measure of uncertainty about the event f. High uncertainty (entropy) is due to a large number of processes, whereas low entropy is due to a small number of dominating processes which make up the time series.

Figure 2:
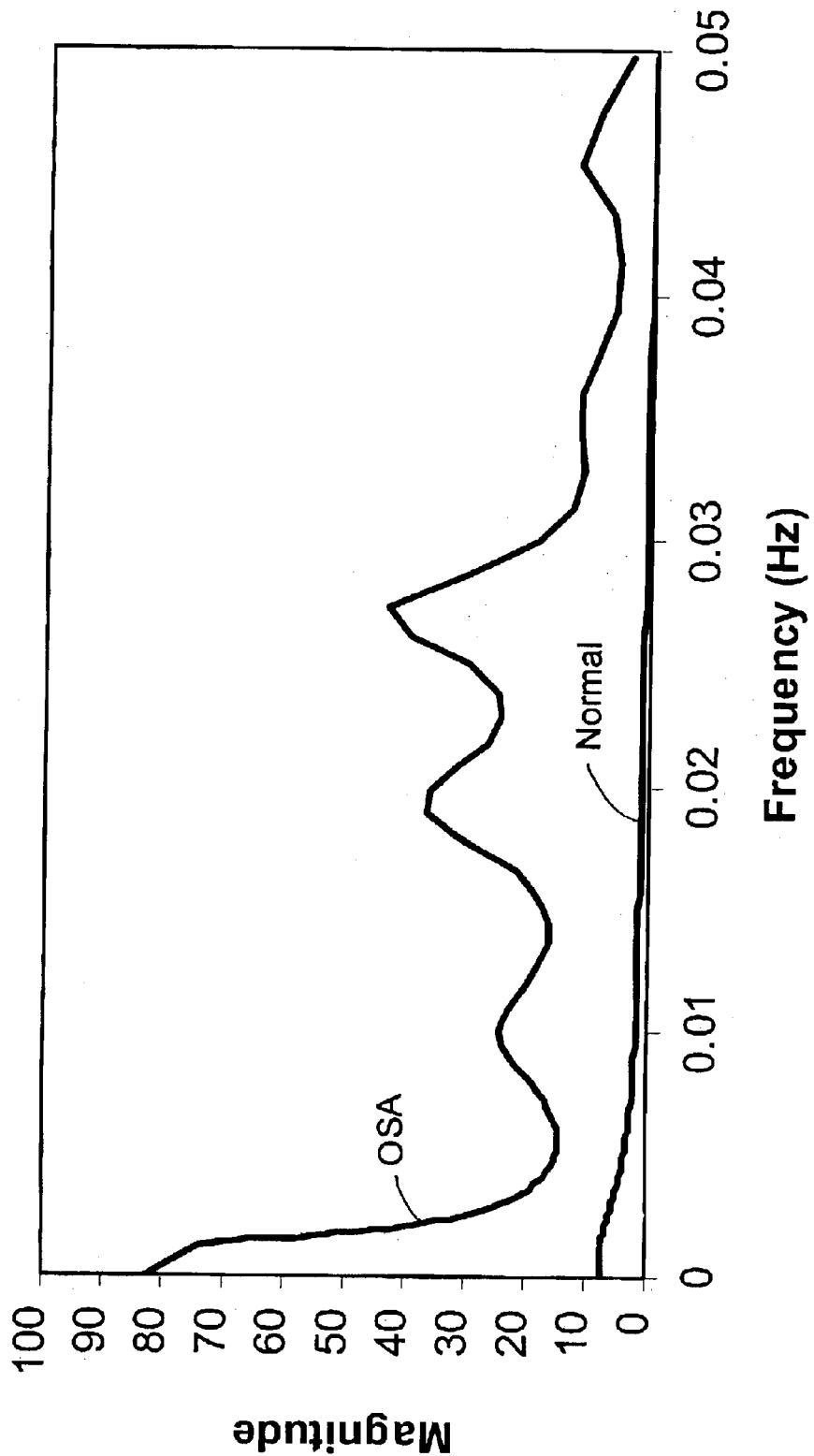
FIG. 2 is a representation of a power spectra of pulse oximetry in two representative patients, one with severe obstructive sleep apnea (OSA; AHI>40/hr) and another without OSA (AHI<5/hr). Magnitude is plotted on the ordinate against frequency on the abscissa. The continuous line is the spectrum of a patient with an apnea-hyponea index less than 5/h and the interrupted line is the spectrum of a patient with an apnea-hyponea index greater than 40/h.
Figure 3:
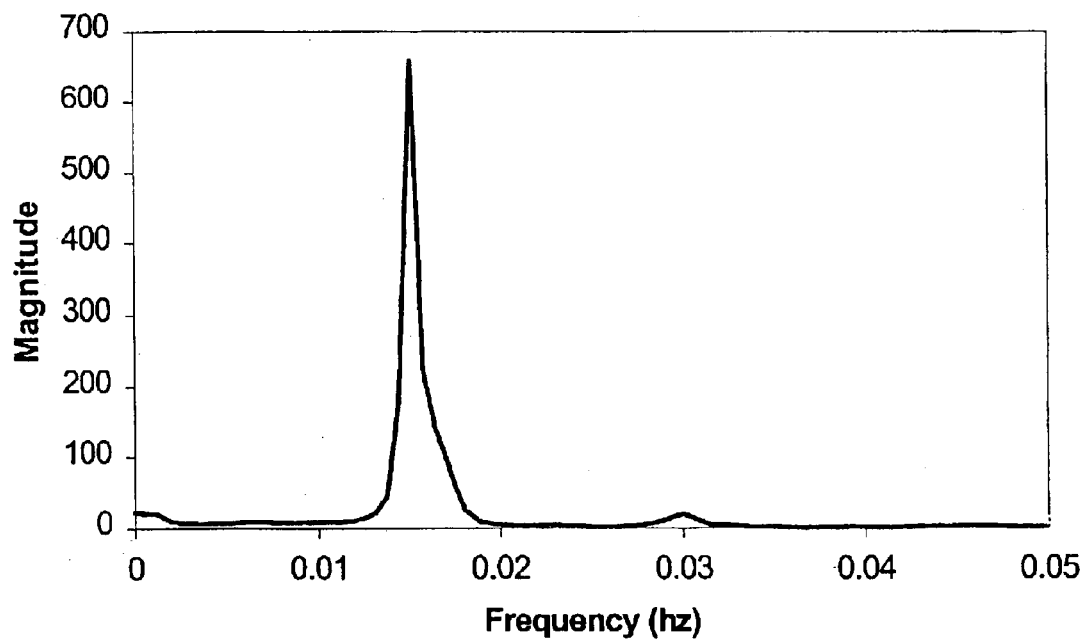
FIG. 3 is a representation of a power spectrum of pulse oximetry in a representative patient with Cheynes-Stokes respiration. Magnitude is plotted on the ordinate against frequency on the abscissa. The ordinate is expanded seven fold compared with FIG. 2.

Representative examples of the power spectra a normal individual, a patient with with OSA, and a patient with CSR are displayed in FIGS. 2 and 3. The power spectrum in CSR patients is characterized by a sharp spectral peak with a large primary local maximum displayed at low frequency (<0.02 Hz). In contrast, the power spectrum in OSA consists of multiple, broad-band spectral peaks, lower in magnitude with the highest local maximum located at a frequency ≧0.02 Hz. In normal subjects, no apparent peak was detected. Table 3 shows the values (mean±SD) of the various indices of the spectral analysis in CSR, OSA patients, and normal controls.

TABLE 3

Summary of the results of spectral analysis

|  | LVF-CSR<br>n = 23 | LVF-No CSR<br>n = 22 | Suspected OSA<br>n = 203 |
|---|---|---|---|
| Magnitude at primary local maximum (ml) | 19 (19.8) | 3.1 (4.6) | 2.18 (0.3) |
| Magnitude at secondary local maximum (m2) | 18 (18.9) | 3.1 (4.6) | 1.88 (0.29) |
| Variance | 8.39 (7.97) | 4.5 (6.8) | 4.82 (7.26) |
| Entropy | 4.44 (0.77) | 4.3 (0.74) | 5.24 (0.77) |

*The results are expressed in terms of means ± SD. LVF is left ventricular failure and CSR is Cheyne Stokes respiration.

In the next step 26, a classification tree was developed with binary recursive partitioning to identify patients with CSR according to the method of Breiman et al. (1984, *Classification and Regression Trees*, Belmont, CA, Wadsworth International Group). In brief, the input data consisted of magnitude and frequency values. The output variable was coded as 1 for the presence of CSR and 0 for the absence of CSR. Because of the preponderance of patients with suspected obstructive sleep apnea, the patients with CSR were weighted by a factor of 10.

The root of the tree is determined by the probability of CSR based on the prevalence in the data set. Next, each variable is selected in turn to determine the most accurate predictor of CSR. The data at the first node is then separated into two branches. At the end of each branch, a new node is developed and the input variables are retested to determine which one produces the most accurate classification into those with CSR and those without. The optimal size of the tree was found by five-fold cross validation.

A receiver operator characteristic (ROC) curve was generated to assess the accuracy of the regression tree. The c-index, which is equivalent to the area under the curve, was used to estimate the diagnostic accuracy of the model. The c-index and its standard error were calculated by the bootstrap method that has been described previously (El-Solh et al., 1996, *Chest*, 110:1299–1304).

Figure 4:
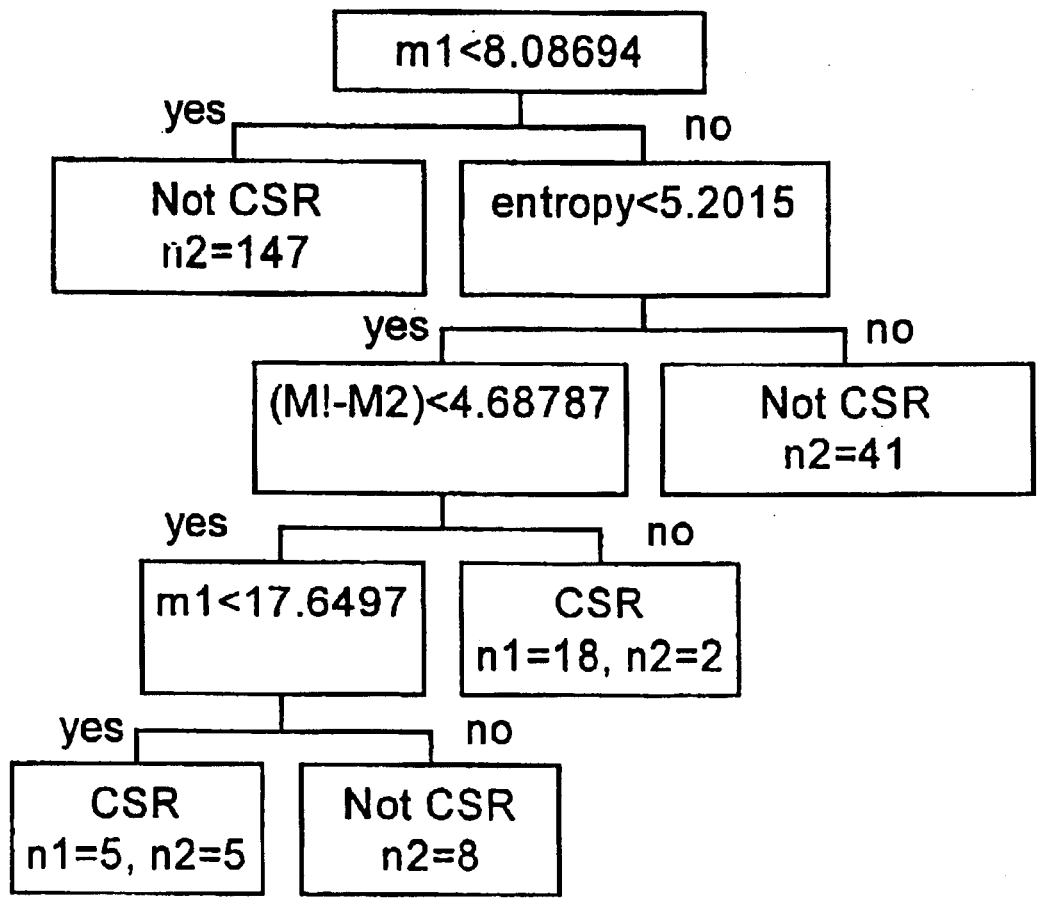
FIG. 4 is a representation of a classification tree to identify patients with Cheyne Stokes respiration (CSR) from the characteristics of the power spectrum of pulse oximetry. M1 and M2 are the magnitudes of the highest and next highest local maximum normalized by the overall variance, m1 is the magnitude of the highest local maximum in absolute terms, n1 is the number of CSR patients and n2 is the number of non CSR patients in a category.
Figure 5:
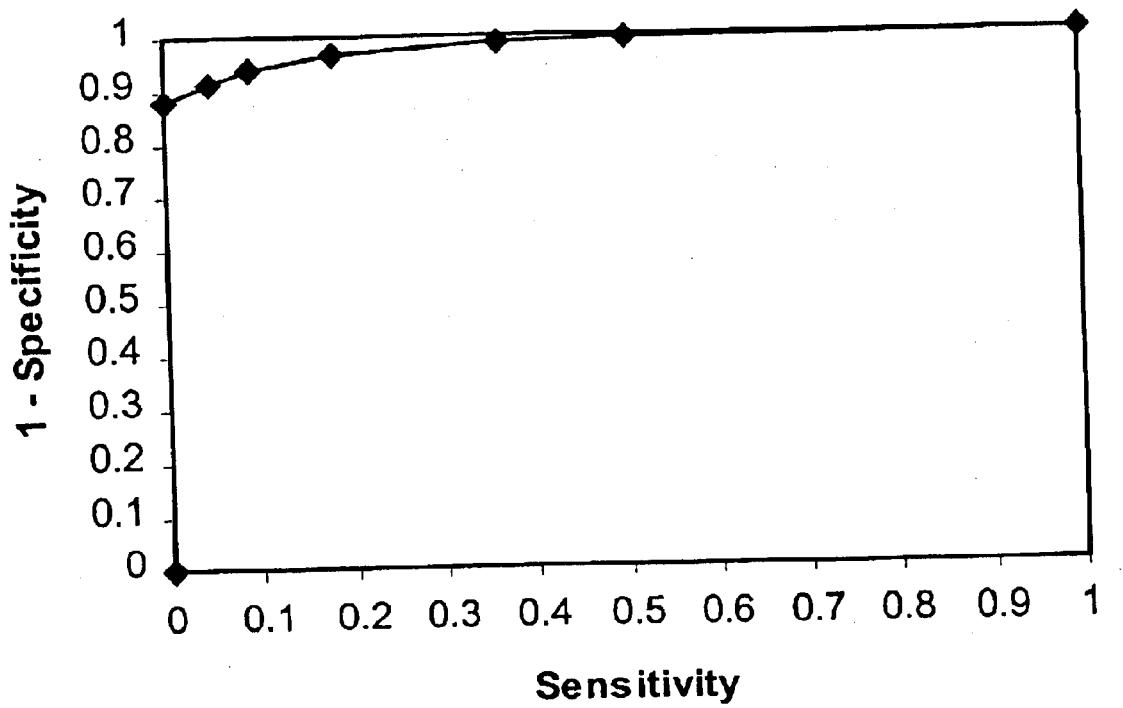
FIG. 5 is a representation of the receiver operator characteristic curve indicating the diagnostic accuracy of the classification tree for identifying patients with Cheyne Stokes respiration from patients suspected of obstructive sleep apnea. Sensitivity is plotted on the ordinate against (1—specificity) on the abscissa.

An example of the classification tree is presented in FIG. 4. The tree was grown by binary recursive partitioning and was shrunk to determine its optimal size using tenfold cross-validation. It was pruned accordingly to avoid overfitting. The tree predicted that CSR was unlikely to be present if the magnitude of the power (m1) at the highest local maximum was less than 8.0867 (%). For those with a local maximum greater than 8.0867, an entropy greater than 5.202 is unlikely to indicate CSR. Of those with a lower entropy, CSR is likely to be present if the difference in the normalized magnitudes between the highest and next highest local maxima was greater than 4.688. Otherwise, CSR will be present only in those with a highest local maximum less than 17.645. When tested on the entire data set, the tree achieved a sensitivity of 100% (95% CI 85%–100%) and a specificity of 97% (95% CI 93%–99%). Seven patients who did not have CSR were classified erroneously as having CSR by the regression tree. The accuracy of the regression tree was assessed with a ROC curve shown in FIG. 5. The c-index, which is equivalent to the area under the curve, was 0.997 (95% CI 0.992–1.0%).

All results are expressed as mean±standard deviation. Differences between patients were compared by the Student's unpaired t test, and frequency events by chi-square test with Yates' correction. All tests of statistical significance were two sided. A p value of 0.05 was considered to be statistically significant. Commercially available software was used to develop the regression tree (S-Plus; Statsci; Seattle, Wash), and for confidence interval (CI) analysis (CIA; *British Medical Journal*; London, England).

To determine the predictive value of the diagnostic method developed as described above, the classification tree constructed as in FIG. 4 was tested on 22 patients with LVF who had no evidence of CSR by overnight polysomnography. Of these 22 patients, two patients were mis-classified as having CSR yielding a specificity of 91 (95% CI: 71–99%) and the positive and negative predictive ratios were 92% (95% CI 74–95%) and 100%(95% CI: 83–100%).

Figure 6:
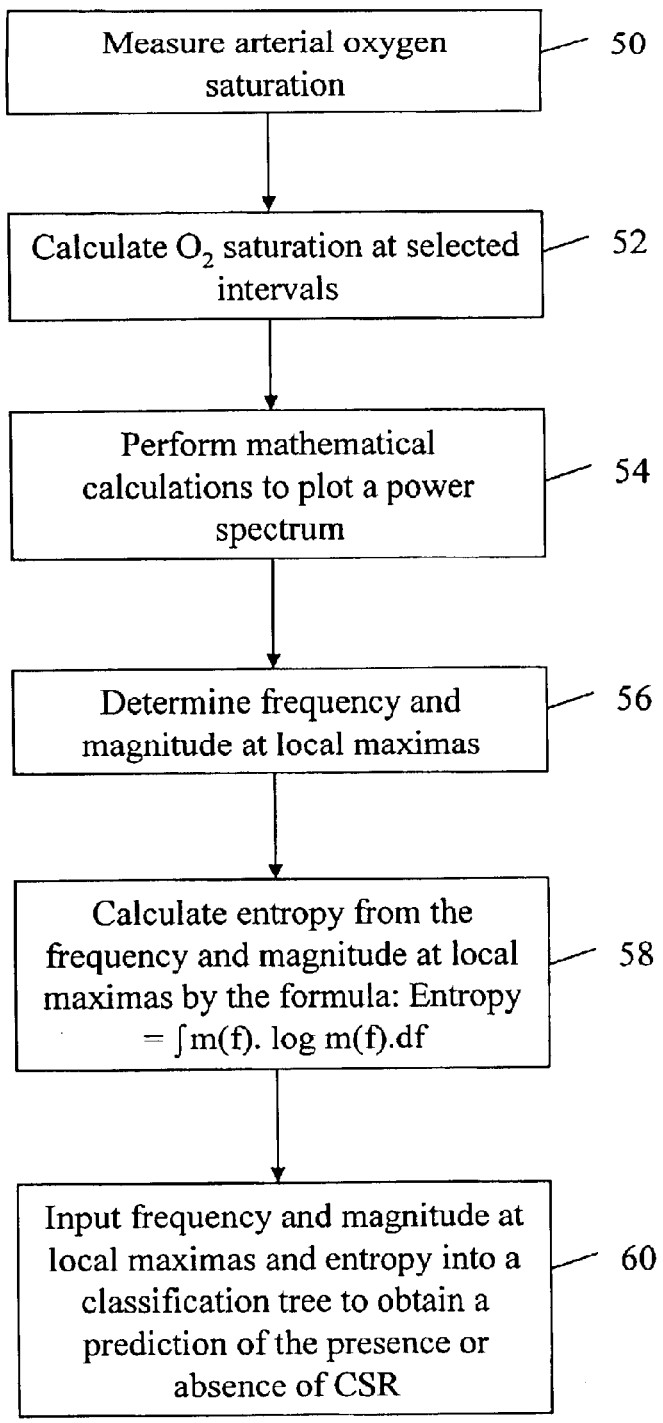
FIG. 6 is a representation of the steps for the diagnosis of CSR in an individual according to the present invention.

In another embodiment of the invention, the classification tree developed as described herein is used in a diagnostic method to identify CSR in an individual. The diagnostic method comprises the steps shown in FIG. 6. Blood oxyhemoglobin saturation levels are obtained from a patient by pulse oximetry recordings (Step 50). Oxygen saturation levels are determined at selected intervals (Step 52). Mathematical calculations are performed to generate a power spectrum (Step 54) from the pulse oximetry readings by plotting magnitude (variance) versus frequency. From the power spectrum, a set of parameters of magnitude and frequency are attained at the highest local maximum (f1, m1) are determined (Step 56). Similarly, the frequency and magnitude of the power attained at the next highest local maxima (f2, m2) are determined. A local maxima of magnitude is identified when there is lower magnitudes at frequencies immediately above and below the particular frequency.

In the next step (step 58), entropy is calculated as described above. In the next step (step 60), the set of parameters and the entropy value determined are input into a classification tree developed as described herein to obtain a prediction of whether the individual has CSR or not.

EXAMPLE 2

This embodiment describes the development of trained neural networks to classify patients as having CSR, OSA or normal breathing. Artificial neural networks (ANN) are computation systems that mimic analytic approach of biologic systems by using a large numbers of interconnected artificial neurons (Cross et al., 1995, *Lancet*, 346, 1075–1079). Just as humans apply knowledge gained from past experience to new problems or situations, a neural network takes previously solved examples to build a system of "neurons" that makes new decisions, classifications, and forecasts. Neural networks look for patterns in training sets of data, learn these patterns, and develop the ability to correctly classify new patterns or to make forecasts and predictions. An artificial neural network for predicting respiratory disturbances is described in U.S. Pat. No. 6,083,173, incorporated herein by reference.

Figure 7:
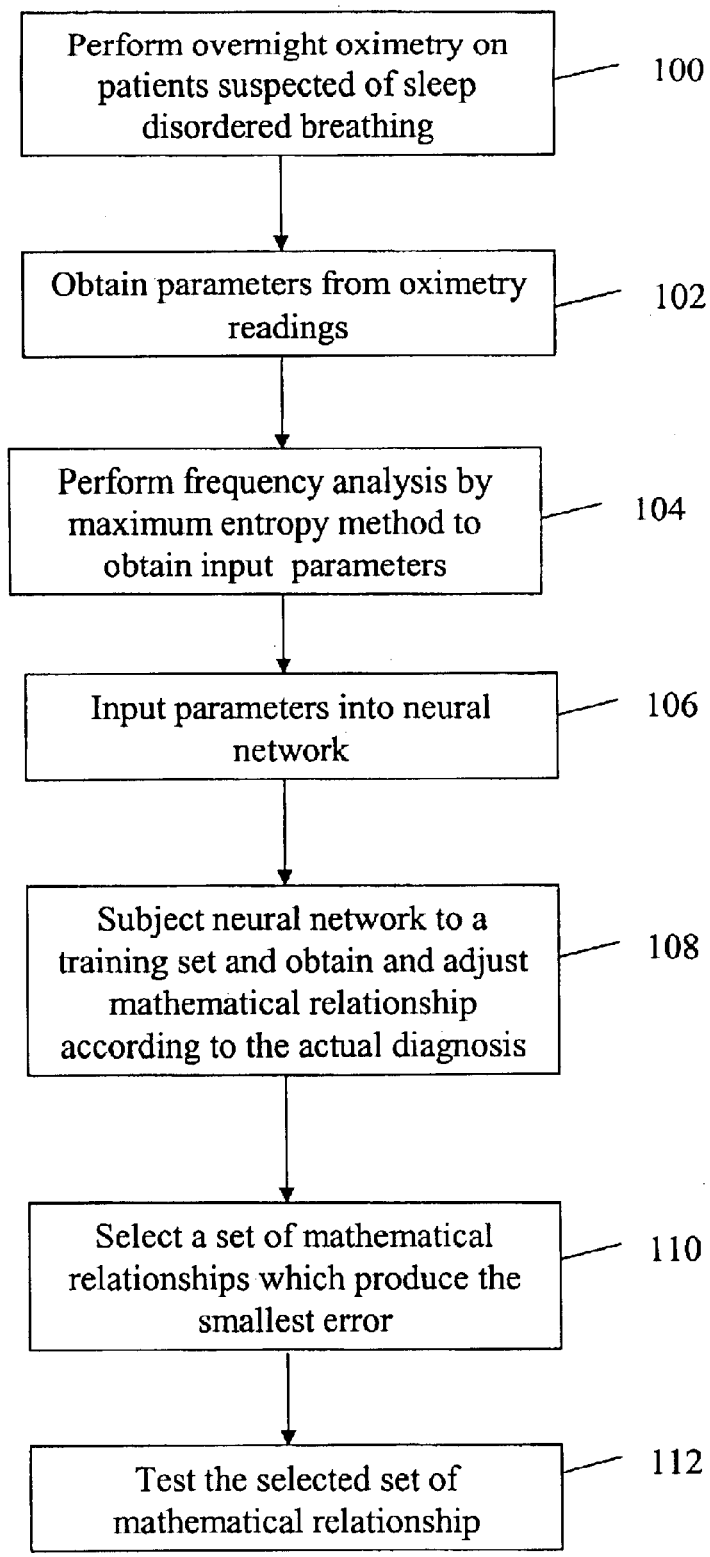
FIG. 7 is a representation of the steps involved in creating a trained neural network.

The construction of the neural network is illustrated in FIG. 7. The method begins by performing overnight oximetry readings on patients suspected of having sleep disordered breathing (step 100). As an example, an analysis of the oximetry recordings of 213 sleep studies conducted between February 1999 and January 2000 referred for evaluation of sleep related breathing disorder. Twenty-three patients had evidence of CSR-CSA, 132 had OSA, and 58 had no evidence of sleep related breathing disorder. The study was approved by the Health Sciences Institutional Review Board of the University at Buffalo.

The sleep studies were conducted at the Veterans Affairs Medical Center of Western New York. Continuous electroencephalogram, electrooculogram, electrocardiogram, submental and anterior tibial electromyogram were recorded on a 16-channel polygraph using standard technique, and digitized on a computerized system (Acquitron®; Mallinckrodt, St. Louis, Mo., and Alice 3®; Respironics, Pittsburgh, Pa.). Airflow was measured qualitatively by an oral-nasal thermistor (EPM Systems, Midlothian, VA). Measurement of arterial oxygen saturation was performed with a pulse oximeter, Nonin 8500™ (Nonin Medical Inc. Plymouth, Minn.), with the probe placed on the patient's finger. Thoracoabdominal movements were recorded using piezoelectric belts.

Sleep stages were scored in 30-sec epochs as described in Example 1. Each epoch was analyzed for the number of apneas, hypopneas, arousals, oxygen desaturation, and disturbances in cardiac rate and rhythm. Apnea was defined as the absence of airflow for more than 10 seconds. An obstructive apnea was defined as the absence of airflow in the presence of rib cage or abdominal excursions. Central apneas were defined by the cessation of airflow for 10 seconds accompanied by an absence of chest wall movement. Hypopnea was defined as a visible reduction in the airflow lasting more than 10 seconds associated with either a 3% decrease in arterial oxygen saturation or an electroencephalographic arousal, or both. Hypopnea was labeled obstructive if paradoxical thoracoabdominal excursions, if the airflow decreased out of proportion to the reduction in the thoracoabdominal excursions, or snoring occurred. The apnea-hypopnea index (AHI) was defined as the number of apneas and hypopneas per hour of sleep. The presence of CSR-CSA was defined as a central apnea-hypopnea index of$\geq$10/hr of sleep in which greater than 85% of events are central, in combination with the characteristic pattern of crescendo-decrescendo pattern of hyperpnea alternating with central apnea. Alternatively, obstructive sleep apnea was defined as all others with AHI >5/hr including those with mixed apneas. Arousals were defined according to the ASDA position paper (The Atlas Task Force, 1992, EEG arousals: scoring rules and examples, *Sleep*, 15:173–184). All sleep studies were reported by one of two board certified sleep physicians. Both sleep physicians who were blinded from each other's opinion reviewed the sleep studies of all patients with CHF to determine the level of agreement in identifying patients with CSR-CSA by polysomnography. Interobserver agreement was assessed by the kappa value. The few discrepancies were resolved by consensus.

In the next step (step 102), various parameters are determined. The lowest value of the oxygen saturation by pulse oximetry over 4 sec intervals was used for spectral analysis. The sampling rate of the pulse oximetry was 70 Hz with a moving average of 3 sec. The data were stored as the average over one-second interval. After the data was decimated into 4 sec intervals, it was processed to remove any artifacts by eliminating all changes of oxygen saturation between consecutive sampling intervals of greater than 4% per second, and any oxygen saturation less than 20%. The data was then divided into segments of 20.84 min long without discontinuities due to artifacts. The length of the segment was selected so that it would contain 10 cycles of the slowest frequency at which CSR-CSA has been recorded (i.e. 0.008 Hz or cycles of 125 sec). Each segment was detrended to reduce the effects of nonlinearities.

In the next step (Step 104) a power spectrum is generated and input parameters are determined. Power spectral density, which represents the distribution of power as a function of frequency, was calculated by the maximum entropy method on each segment as described in Example 1. The Bayesian information criterion was chosen to select the model order. The power spectrum was calculated at 100 equidistant frequencies on logarithmic scale ranging from 0.0008 Hz to 0.04 Hz. At each frequency, the mean power was calculated from the average of the power of all segments at that particular frequency. The salient features of the CSR-CSA power spectrum that were selected for further analysis were the frequency and the magnitude of the power attained at the highest local maximum (f1, m1), and the frequency and the magnitude of the power attained at the next highest local maximum (f2, m2). The randomness of the variability in oxygen saturation was estimated from the entropy calculated as described in Example 1.

Oxygen desaturation events for 2%, 3%, and 4% were calculated from overnight oximetry. The definition of a desaturation event was based on the work of Taha and colleagues (1997, *Sleep*, 20, 991–1001). Every data point was examined sequentially to determine if criteria were met to define an event. The criteria for an event were a decrease of at least the set amount (2%, 3%, or 4%) in oxygen saturation from the initial data value for at least 10 sec, and at a rate that is greater than 0.1% sec. In addition, the oxygen saturation must return within 60 sec to within 1% of the initial value, or increase from its nadir by 1.5 times or more of the set amount of the dip. Once the criteria were met, a new search for an event was initiated at the next data point after the event. The data derived from the spectral analysis, i.e., the frequency and the magnitude at the highest and the next highest local maxima were used along the delta index as input to the neural network.

In the next step (step 106), a probabilistic neural network (PNN) was used. These networks are type of supervised networks known for their ability to train quickly on sparse datasets and separate data into a specified number of output categories. The PNN is a three layer-network: an input layer, a hidden layer, and an output layer. The input layer included the salient features of the spectral analysis. These features comprised of the frequency and the magnitude attained at the highest local maximum; the frequency and the magnitude of the power attained at the next highest local maximum; and the randomness of the variability in oxygen saturation. Other input variables included the desaturation events for 2%, 3%, and 4% and the delta index.

Another variable for the input layer was the delta index introduced by Pepin and colleagues (1991, *Chest*, 99, 1151–1157) to compute oxygen saturation (SaO2) oscillation associated with sleep apneas. Many patients who have sleep apnea experience several hundred apneas or hypopneas each night without significant SaO2 desaturations. They will however overtime demonstrate small changes or oscillations in their SaO2. The index measures the variation between successive data at constant time intervals. If saturation is nearly constant during the night, delta index (Δ) will be very low, as SaO2 variation will be minimal. Even if saturation is decreased gradually, corresponding to prolonged desaturations as are found in COPD, only a few intervals will exhibit a high variation. In this case, delta index will be low. On the other hand, the SaO2 profile for the night in sleep apnea is due to a nearly continuous apnea-resumption of ventilation sequence which leads to wide SaO2 oscillations, hence a high delta index. The delta index is calculated using the following formula:

$$\Delta = 1/n \Sigma |(\delta(SaO_2)/\delta(t)|$$

wherein δ=change in $SaO_2$, n=number of intervals, and t=time.

All independent variables were scaled to a value over a range of 0 to 1 to normalize inputs. Because of the preponderance of patients with OSA, patients with CSR-CSA were weighted by a factor of 5.

The hidden layer is an intervening layer of processors that detect higher-order features in the input layer, analyze the signal, and relay the output to other neurons to make a correct response. The number of neurons in the hidden layer is determined by the number of patterns in the training set as PNN requires one neuron per pattern processed. The number of hidden units or neurons of our PNN was derived from the total number of patterns minus the evaluation set.

The number of hidden units was derived from the total number of patterns minus the evaluation set. The output layer provides a classification of the input patterns into three groups: CSR-CSA, OSA, or no sleep related breathing disorder.

In the next step (step 108), the neural network is exposed to a training set and adjusted according to the actual diagnosis of CSR, OSA or no breathing disorder obtained by polysomnography studies follow up on the patients. Because of the preponderance of patients with obstructive sleep apnea, patients with CSR-CSA were weighted by a factor of 5. A five-fold cross validation was used for evaluation. The data were divided randomly into five mutually exclusive subsets. Four of the subsets were pooled and used for training; the remaining subset was used as an evaluation set during training. The entire process was repeated four additional times by rotating the subset that was used as the evaluation set during training. For each model a kappa value was obtained to assess reproducibility. In the next step (step 110) the neural network closest to the median was selected for further analysis.

In the next step, the trained neural network as obtained above was tested on patients (step 112). Review of medical records revealed that all 23 cases with CSR-CSA had evidence of systolic dysfunction with a mean left ventricular ejection fraction of 25.0±8.4, and were considered for heart transplantation. All were receiving optimal oral therapy and were clinically stable at the time of the sleep study. Of the 132 patients with polysomnographic evidence of OSA, 39 (30%) had severe OSA with AHI >30/hr, 35 (27%) had moderate OSA with AHI ranging between 15 and 30/hr, and 58 (43%) had mild OSA with AHI between >5 and <15/hr. There was excellent agreement between the two physicians in interpreting the overnight polysomnography with a kappa of 0.84±0.14SE. There were only four discrepancies all of which were resolved by consensus meetings.

The power spectrum for CSR-CSA patients was similar to one shown in FIG. 2 and is characterized by a sharp spectral peak with a large primary local maximum displayed at low frequency (<0.02 Hz). In contrast, the power spectrum in OSA consists of multiple, broadband spectral peaks that are lower in magnitude, with the highest local maximum located at a frequency >0.02 Hz. In normal subjects, no apparent peak was detected as shown in FIG. 3.

The predictive accuracy of the PNN in detecting CSR-CSA achieved a sensitivity of 100% (95% CI: 85% to 100%) and a specificity of 99% (95% CI: 97% to 100%) (table 4). The neural network was able to identify accurately all cases who had CSR-CSA. In total, there were three misclassifications. One patient with OSA was predicted to have CSR-CSA, and two with OSA were mislabeled as having no sleep related disordered breathing. The patient with OSA misclassified to have CSR-CSA had AHI of 38 while the two patients reported as having no sleep related disordered breathing had an AHI of 6 and 9, respectively.

TABLE 4

Classification of neural network output

|  | CSR-CSA | OSA | No sleep disorder |
|---|---|---|---|
| Actual | 23 | 132 | 59 |
| Predicted | 24 | 129 | 61 |
| True positives | 23 | 129 | 59 |
| False positives | 1 | 0 | 2 |
| True negatives | 190 | 82 | 153 |
| False negatives | 0 | 3 | 0 |

Figure 8:
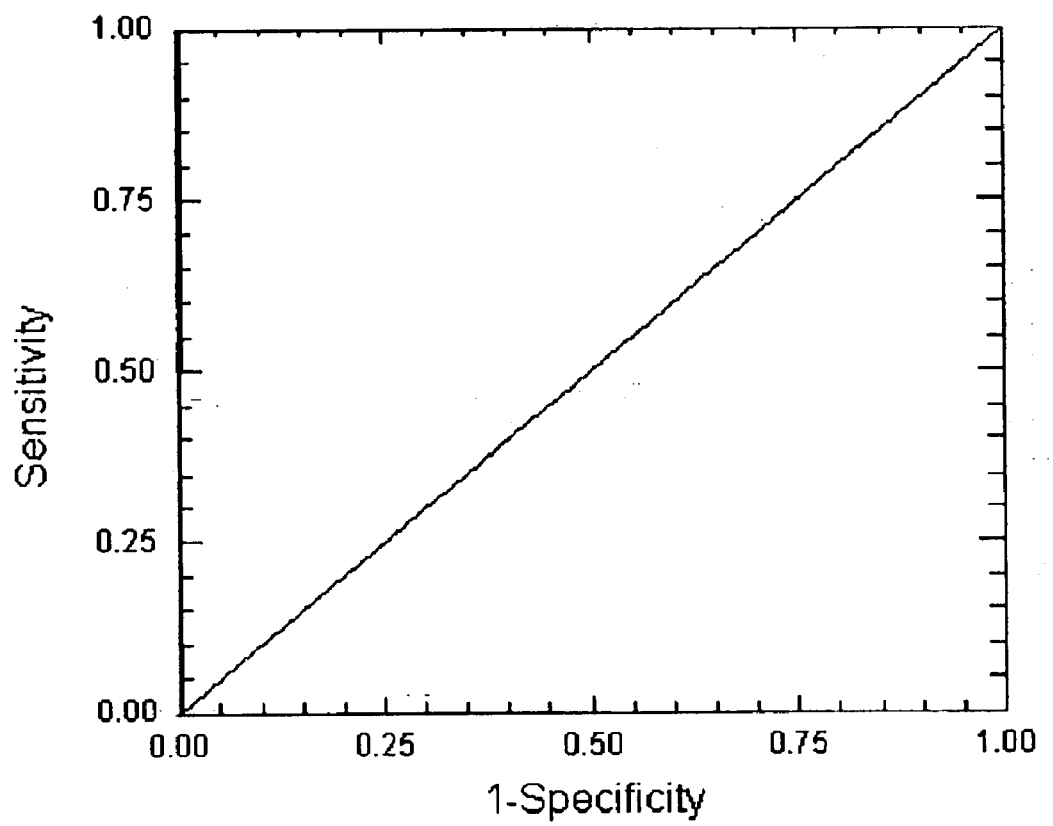
FIG. 8 is a representation of a receiver operator characteristic curve of the diagnostic accuracy of the neural network Sensitivity is plotted against (1—specificity).

A receiver operator characteristic (ROC) curve was generated to assess the accuracy of the neural network. The c-index, which is equivalent to the area under the ROC curve, was used to estimate the diagnostic accuracy of the model. The c-index and its standard error were calculated by the bootstrap method (22). Kappa statistics were calculated from software available in the public domain (23). The results are shown in FIG. 8.

EXAMPLE 3

Figure 9:
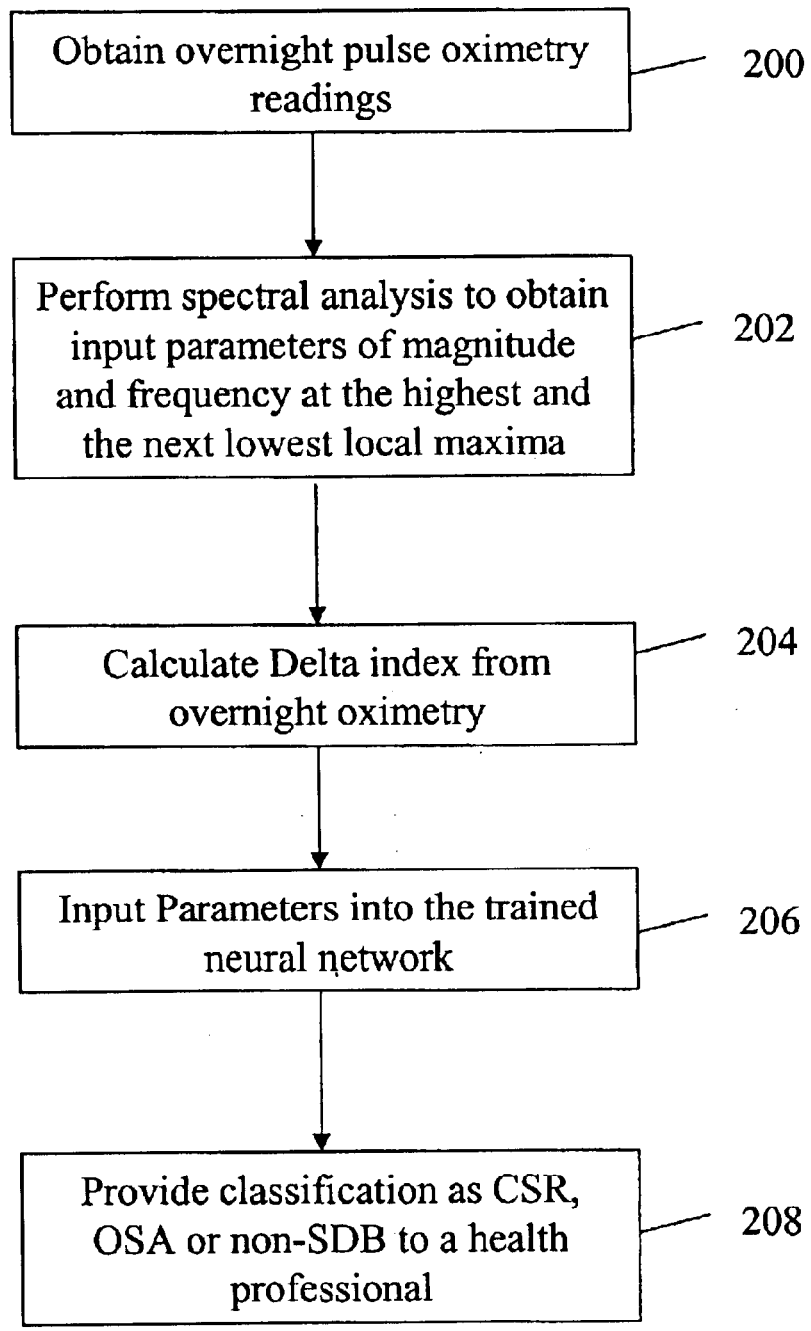
FIG. 9 is a representation of the steps involved in classifying a patient as having CSR, OSA or no breathing disorder.

This embodiment describes the use of the trained neural network for diagnosis of patients as having CSR, OSA or no sleep breathing disorder. The steps of this method are shown in FIG. 9. To use the trained neural network, overnight oximetry readings are performed on patients suspected of having a respiratory condition (step 200). Any artifacts are searched and eliminated. It is preferable to verify that there is sufficient duration of record without artifact for analysis. The number of desaturation events/hour to 2, 3% and 4% below baseline values are calculated. Then the cumulative time as percent of recording time that oxygen saturation is below selected values (such as 90, 88, 86, 84, 82 and 80%) is calculated. Frequency analysis is performed by maximum entropy method. The highest (M1) and second highest (M2) peaks of power are identified and the magnitudes and frequency at which they occur are determined (Step 202). The delta index is calculated as described in Example 2 (Step 204). Next, input parameters are determined (Step 206). The values for M1–M2 and M2/M1 are calculated. The entropy in the frequency spectrum over the range of 0.04 to 0.5 Hz is calculated and then the trained neural network is used to identify classification as CSR, OSA or no disordered breathing (Step 208).

From the foregoing, it will be obvious to those skilled in the art that various modifications in the methods described herein can be made without departing from the spirit and scope of the invention. Accordingly, the invention may be embodied in other specific forms without departing from the essential characteristics thereof. The embodiments and examples presented herein are therefore to be considered as illustrative and not restrictive.

What is claimed is:

1. A method for detecting Cheyne-Stokes respiration in an individual comprising:

obtaining pulse oximetry recordings from the individual;

determining oxygen saturation levels at selected intervals;

generating a power spectrum from the oxygen saturation levels;

determining a set of parameters from the power spectrum and the oximetry readings, wherein the set of parameters comprises a delta index; and inputting the set of parameters into a trained neural network to classify an individual as having Cheyne-Stokes respiration, obstructive sleep apnea or no sleep disordered breathing.

2. The method of claim 1, wherein the pulse oximetry readings are obtained overnight.

3. The method of claim 1, wherein the set of parameters from the power spectrum comprise frequency and magnitude of highest and second highest peaks at local maximas.

4. A storage device having stored thereon computer readable code for causing a computer to execute the method of claim 1.

5. The storage device of claim 4, selected from the group consisting of a floppy disk, a hard drive, a compact disc and a zip drive.

6. A method for developing a trained neural network for classification of an individual as having CSR, OSA or no sleep breathing disorder comprising the steps of:

performing clinical studies to identify patients as having Cheyne-Stokes respiration, obstructive sleep apnea or no sleep breathing disorders;

obtaining overnight pulse oximetry recordings from the patients;

generating power spectra from the oxygen saturation levels;

determining a set of parameters from the power spectra and from the pulse oximetry readings;

analyzing the parameters to obtain relationships between the parameters;

expressing the relationships mathematically; and exposing the mathematical relationships to a training set and adjusting the mathematical relationships to produce a desired effect.

7. The method of claim 6 further comprising the step of cross-validating the trained neural network.

8. The method of claim 6, wherein the clinical studies are polysomnography studies.

* * * * *